(12) United States Patent  (10) Patent No.: US 7,564,998 B2
Tsujii  (45) Date of Patent: Jul. 21, 2009

(54) IMAGE PROCESSING APPARATUS AND METHOD, AND PROGRAM

(75) Inventor: Osamu Tsujii, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 504 days.

(21) Appl. No.: 11/102,661

(22) Filed: Apr. 11, 2005

(65) Prior Publication Data

US 2005/0226486 A1 Oct. 13, 2005

(30) Foreign Application Priority Data

Apr. 12, 2004 (JP) ............................. 2004-117058

(51) Int. Cl.
*G06K 9/00* (2006.01)
(52) U.S. Cl. .................................... 382/128
(58) Field of Classification Search ............. None
See application file for complete search history.

(56) References Cited

U.S. PATENT DOCUMENTS

| | | | | |
|---|---|---|---|---|
| 5,825,908 A | * | 10/1998 | Pieper et al. | 382/131 |
| 5,832,134 A | * | 11/1998 | Avinash et al. | 382/257 |
| 6,466,813 B1 | * | 10/2002 | Shukla et al. | 600/411 |
| 6,609,021 B1 | * | 8/2003 | Fan et al. | 600/425 |
| 2002/0028008 A1 | * | 3/2002 | Fan et al. | 382/131 |
| 2003/0190010 A1 | | 10/2003 | Tsujii | 378/23 |
| 2005/0147285 A1 | | 7/2005 | Tago et al. | 382/130 |

FOREIGN PATENT DOCUMENTS

| | | | |
|---|---|---|---|
| JP | 07-236634 | A | 9/1995 |
| JP | 07-265300 | A | 10/1995 |
| JP | 08-066392 | A | 3/1996 |
| JP | 08-166995 | A | 6/1996 |
| JP | 2001-137230 | A | 5/2001 |
| JP | 2002-078706 | A | 3/2002 |

OTHER PUBLICATIONS

Feldkamp, L.A., et al., "Practical Cone-Beam Algorithm," J. Opt. Soc. Am. A, vol. 1, No. 6 (1984), pp. 612-619.
"Lung Cancer Screening CT (LSCT) Diagnosis Aiding System," Journal of Computer Aided Diagnosis of Medical Images (CADM), vol. 2, No. 3 (1998).
Jain, A.K., "*Fundamentals of Digital Image Processing*," Prentice Hall (1989), pp. 380-391.

* cited by examiner

*Primary Examiner*—Matthew C Bella
*Assistant Examiner*—Alex Liew
(74) *Attorney, Agent, or Firm*—Fitzpatrick, Cella, Harper & Scinto

(57) ABSTRACT

A first cross section image other than an axial image of a subject is generated from a radiation image. A nodule in the first cross section image is detected. A second cross section image including the detected nodule is generated from the radiation image. A feature amount of the second cross section image is calculated. It is determined based on the calculated feature amount whether not the detected nodule is a diagnostic pathology. A diagnostic image including the detected nodule is output on the basis of the determination result.

9 Claims, 7 Drawing Sheets

IMAGE PROCESSING APPARATUS AND METHOD, AND PROGRAM

FIELD OF THE INVENTION

The present invention relates to an image processing apparatus and method for processing a radiation image of a subject acquired utilizing radiation, and outputting a diagnostic image, and a program.

BACKGROUND OF THE INVENTION

Conventionally, an X-ray CT apparatus which irradiates a subject with X-rays, detects X-rays transmitted through or scattered by the subject using an X-ray detector, and makes a fluoroscopic image, tomosynthesis, or three-dimensional (3D) image on the basis of this X-ray detection output (the number of photons of X-rays) is known.

As such X-ray CT apparatus, a cone beam CT apparatus has been developed. In a normal X-ray CT apparatus, an X-ray beam is limited to be thin in the Z-direction, and is called a fan beam. However, cone beam CT (CBCT) uses an X-ray beam which also spreads in the Z-direction, and is called a cone beam.

In multi-slice CT or CBCT, images are generated in large quantities as imaging results. Hence, a diagnosis aiding device for a doctor, which selects and presents images suited for diagnosis from the images in large quantities, becomes important. Especially, detecting a nodule from a chest CT image from which a pathology is relatively easily detected meets a requirement upon using CT in the medical examination purpose. Conventionally, many researchers have made studies about detection of a nodule from an axial image.

For example, a specific region (nodule) used to determine whether or not it is a tumor is extracted from two-dimensional (2D) image (axial) information, an area S of that region is calculated, and the centroid of the extracted region is calculated. A radius r of a circle having the same area as the extracted region (to be referred to as an equivalent radius of the extracted region hereinafter) is calculated by:

$$r=(S/\pi)^{1/2} \quad (1)$$

Next, the circularity of the extracted region is calculated. The circularity is defined using the calculated centroid as the center on the basis of the ratio of the area of the extracted region included in the circle of the calculated equivalent radius r by:

$$\text{Circularity} = \text{area of extracted region included in circle}/S \quad (2)$$

In a feature space determined by the equivalent radius r and circularity, if the equivalent radius r and circularity are included in a given range, it is determined that the extracted region is a tumor.

Japanese Patent Laid-Open No. 07-236634 has proposed the following apparatus. That is, regions are extracted from a large number of pieces of 2D image information which are distributed three-dimensionally in place of only one image, and the equivalent radii and circularities of the extracted regions are calculated. Then, tumors are detected for respective images on the basis of the circularities.

Japanese Patent Laid-Open No. 08-066392 has proposed a diagnosis aiding system comprising:

a first processing function of obtaining an image of interest by extracting density data values of CT images obtained by reconstruction using a desired first threshold value with a low density data value;

a first determination function of determining based on a feature amount such as a shape or the like of the extracted image of interest if the image of interest is a nodule;

a second processing function of obtaining an image of interest by extracting density data values of CT images using a desired second threshold value with a high density data value;

a candidate determination function of determining based on a feature amount such as a shape or the like of the extracted image of interest if the image of interest can be a candidate of a nodule;

a third processing function of acquiring an enlarged CT image of a predetermined scale by reconstructing the image of interest determined as the candidate by zooming from projection data, and extracting the enlarged CT image using the first threshold value to obtain an image of interest; and a second determination function of determining based on a feature amount such as a shape or the like of the image of interest extracted in the third processing function if the image of interest is a nodule.

Japanese Patent Laid-Open No. 08-166995 has proposed a medical diagnosis aiding system which calculates a plurality of CT images from projection data obtained by projecting a 3D region of a patient, and provides information used to aid diagnosis of the patient on the basis of the plurality of CT images via an output device. This medical diagnosis aiding system comprises a CT image analysis means for determining a CT image suspected to be an affected area from the plurality of CT images as an image of interest, and a display control means for controlling the output device to display a plurality of first 2D images of a 3D region corresponding to the image of interest, which are emphasized from a plurality of second 2D images of the remaining 3D region.

Japanese Patent Laid-Open No. 2001-137230 has proposed a computer-aided diagnosis system comprising:

a region extraction unit for extracting a region of a specific organ from multi-slice first CT images and multi-slice second CT images which have a different imaging timing from the first CT images in association with the same portion of the same patient as the first CT images; and a slice matching unit for matching an anatomical position associated with the body axis direction between the first and second CT images on the basis of indices associated with the sizes and shapes of the regions of the specific organ, which are extracted from the first and second CT images.

Japanese Patent Laid-Open No. 2002-078706 has proposed a computer-aided diagnosis method for aiding diagnosis using 3D digital image data.

This computer-aided diagnosis method comprises:

a step of identifying a 3D object in 3D digital image data;

a step of calculating a local rotation plane for one predetermined 3D object, the local rotation plane being centered about the centroid of the predetermined object and a local rotation axis;

a step of rotating the local rotation plane through at least a partial angle of 360°; and a step of obtaining a plurality of observation images of the predetermined object by generating observation images of the predetermined object in prescribed increments of rotation.

All the aforementioned references have proposed techniques in which the image to be processed is based on an axial image. Conventionally, primary detection for detecting a nodule having a nearly circular shape is done on the basis of an axial image, and the nodule is determined based on the connectivity of candidates in other neighboring axial images.

As diagnosis aiding techniques using coronal images other than axial images, for example, a diagnosis aiding apparatus that utilizes a plurality of axial images has been proposed as Japanese Patent Laid-Open No. 7-265300. This diagnosis aiding apparatus comprises a means for extracting a region of interest from at least one of the plurality of axial images, and means for generating a plurality of coronal images by applying multi-planar reconstruction to images in the region of interest extracted by the extraction means of the plurality of axial images, and is wherein the plurality of axial images are used in diagnosis.

According to Japanese Patent Laid-Open No. 7-265300, coronal images are calculated by applying multi-planar reconstruction to only the region of interest of the axial images, and diagnosis is made using the coronal images. Hence, the number of images to be interpreted by the doctor can be reduced compared to axial images to be interpreted.

The reason why CAD processes are conventionally done based on axial images is that continuity in the body axis direction is not guaranteed before spiral CT. For this reason, artifacts are generated due to connection errors in the body axis direction if multi-planar reconstruction is made.

In Multi detector row spiral CT in recent years, roughly isotropic images can be constructed but are not perfect since spiral scan is done. By contrast, in CBCT that scans organs such as lungs by one revolution, since perfect isotropy is guaranteed, perfect coronal images can be generated.

On the other hand, since vein branches in lungs normally run in the up-and-down direction, a roughly circular nodule detected from an axial image is readily mistaken for a vein, resulting in no advantages.

SUMMARY OF THE INVENTION

The present invention has been made to solve the aforementioned problems, and has as its object to provide an image processing apparatus and method which can precisely and quickly determine and output diagnostic images including a diagnostic pathology from subject images, and a program.

According to the presenting invention, the foregoing object is attained by providing an image processing apparatus for processing a radiation image of a subject obtained by utilizing radiation, and outputting a diagnostic image, comprising:

first generation means for generating a first cross section image of a first cross section other than an axial cross section of the subject from the radiation image;

detection means for detecting a nodule in the first cross section image;

second generation means for generating a second cross section image of a second cross section other than the first cross section of the subject from the radiation image, and wherein the second cross section image includes the nodule detected by said detection means;

calculation means for calculating a feature amount of the second cross section image;

determination means for determining based on the feature amount calculated by the calculation means whether or not the nodule detected by the detection means is a diagnostic pathology; and output means for outputting a diagnostic image including the nodule detected by the detection means on the basis of a determination result of the determination means.

In a preferred embodiment, the first cross section image is one of a coronal image, sagittal image, and RAYSUM image thereof of the subject.

In a preferred embodiment, the second cross section image is an axial image of the subject.

In a preferred embodiment, when the first cross section image is a coronal image of the subject, the second cross section image is one of an axial image and sagittal image of the subject.

In a preferred embodiment, a 3D voxel reconstructed from the radiation image is formed of isotropic pixels.

In a preferred embodiment, the calculation means calculates a circularity of the nodule in the second cross section image as the feature amount.

In a preferred embodiment, the apparatus further comprises:

image sensing means for irradiating the subject with radiation, and sensing and outputting the radiation image of the subject.

According to the present invention, the foregoing object is attained by providing an image processing method for processing a radiation image of a subject obtained by utilizing radiation, and outputting a diagnostic image, comprising:

a first generation step of generating a first cross section image of a first cross section other than an axial cross section of the subject from the radiation image;

a detection step of detecting a nodule in the first cross section image;

a second generation step of generating a second cross section image of a second cross section other than the first cross section of the subject from the radiation image, and wherein the second cross section image includes the nodule detected in said detection step;

a calculation step of calculating a feature amount of the second cross section image;

a determination step of determining based on the feature amount calculated in the calculation step whether or not the nodule detected in the detection step is a diagnostic pathology; and an output step of outputting a diagnostic image including the nodule detected in the detection step on the basis of a determination result in the determination step.

According to the present invention, the foregoing object is attained by providing a program for implementing image processing for processing a radiation image of a subject obtained by utilizing radiation, and outputting a diagnostic image, comprising:

a program code of a first generation step of generating a first cross section image of a first cross section other than an axial cross section of the subject from the radiation image;

a program code of a detection step of detecting a nodule in the first cross section image;

a program code of a second generation step of generating a second cross section of a second cross section other than the first cross section of the subject from the radiation image, and wherein the second cross section image includes the nodule detected in said detection step;

a program code of a calculation step of calculating a feature amount of the second cross section image;

a program code of a determination step of determining based on the feature amount calculated in the calculation step whether or not the nodule detected in the detection step is a diagnostic pathology; and a program code of an output step of outputting a diagnostic image including the nodule detected in the detection step on the basis of a determination result in the determination step.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DETAILED DESCRIPTION OF THE PREFERRED EMBODIMENTS

Preferred embodiments of the present invention will now be described in detail in accordance with the accompanying drawings.

The present invention relates to a radiation image sensing technique for imaging a radiation distribution in a subject using radiation such as an X-ray CT apparatus that makes an image using radiation such as X-rays and the like. More particularly, the present invention relates to a cone beam CT apparatus having a computer diagnosis aiding function or an image processing technique having a computer-aided diagnosis processing function from cone beam CT images.

Figure 1:
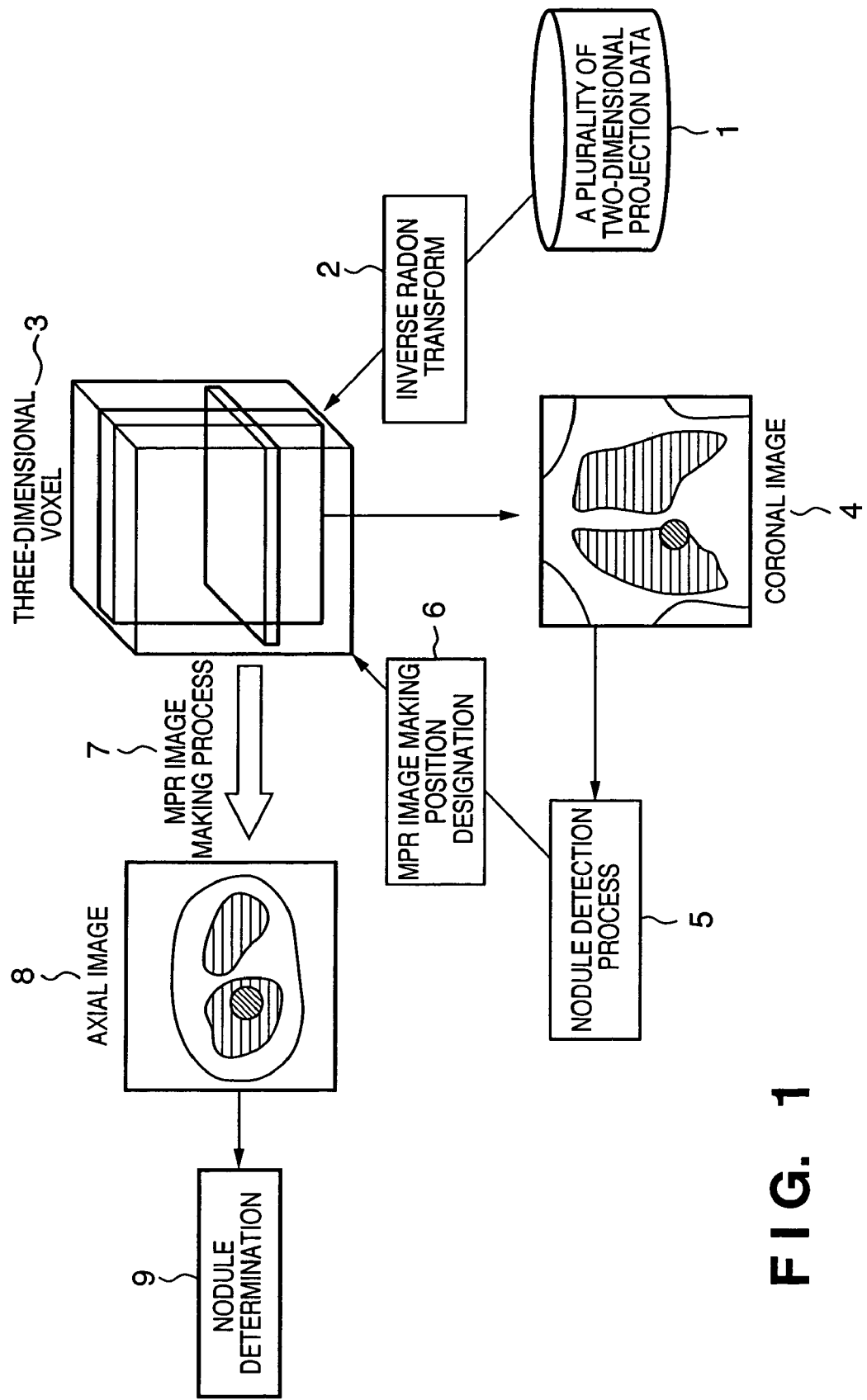
FIG. 1 is a schematic view for explaining the overall picture of an image processing system according to the present invention.

FIG. 1 is a schematic view for explaining the overall picture of an image processing system according to the present invention.

For example, a 3D voxel 3 as a 3D image of a subject is reconstructed by computing inverse radon transforms (2) of a plurality of 2D projection data through 360° (or 180°+fan angle) of the subject obtained from a CBCT imaging apparatus.

In FIG. 1, images from the CBCT apparatus are to be processed. However, the present invention is not limited to such specific image as long as a CT apparatus can output images which are constructed by pixels for which perfect isotropy is guaranteed (isotropic pixels).

A coronal image 4 is generated from the 3D voxel by multi-planar reconstruction (MPR). As the coronal image 4, a plurality of coronal images from the back to the front or vice versa of the subject are sequentially generated. Note that the thickness upon generating the coronal images 4 is set in advance depending on the size of a nodule to be detected.

A nodule detection process 5 is applied to the coronal images 4. In order to make axial images (MPR images) including nodule candidates detected by the nodule detection process 5 from the 3D voxel 3, a MPR image making position designation process 6 is executed.

A feature amount of a corresponding nodule is calculated for axial images 8 made from the 3D voxel 3 at the designated MPR image making position by a MPR image making process 7. A true/false determination process 9 for determining whether or not the nodule is a diagnostic pathology (e.g., a disease, tumor, or the like) is executed on the basis of the calculation result.

An example of the arrangement of the image processing system according to this embodiment will be explained using FIG. 2.

Figure 2:
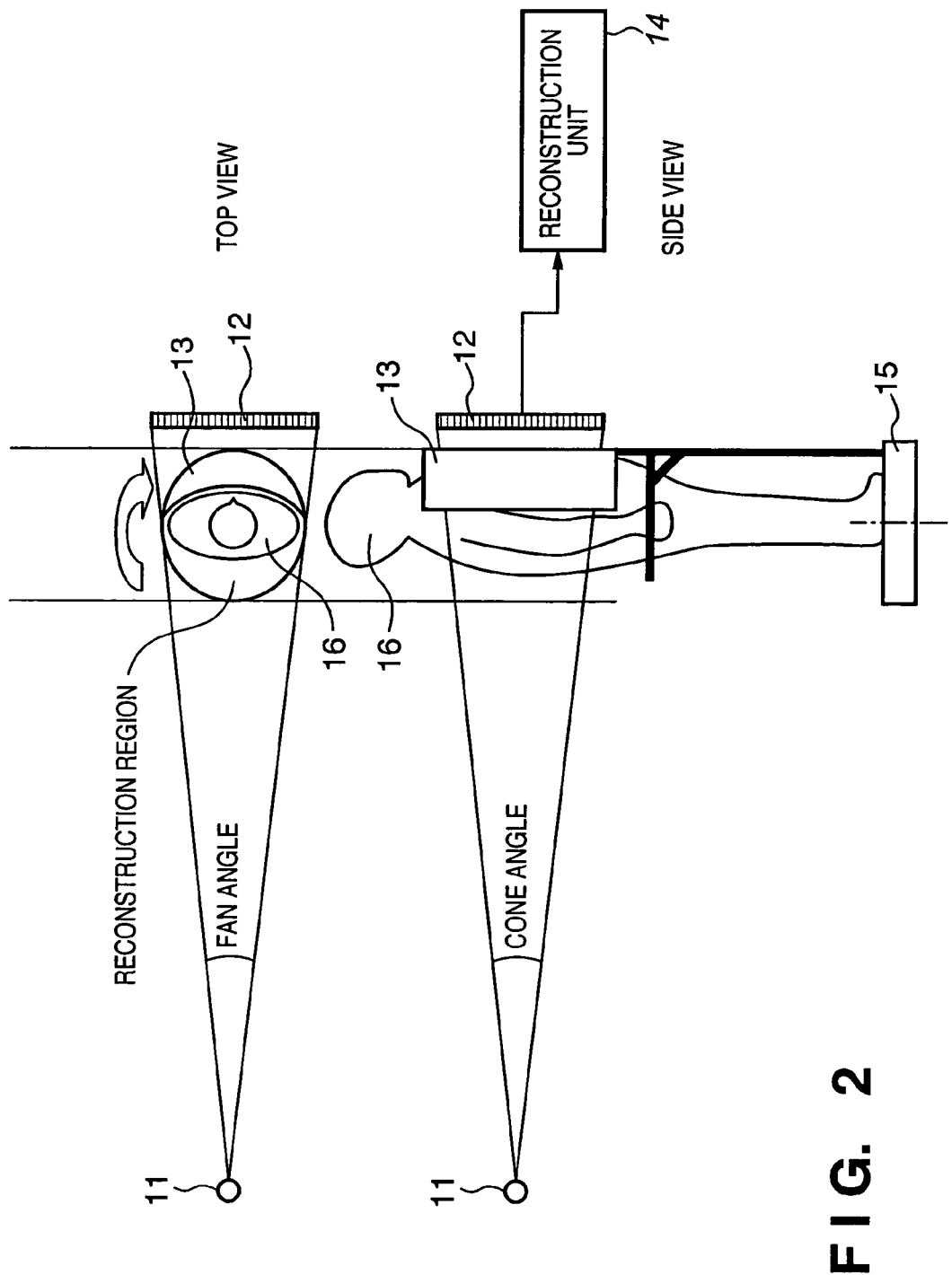
FIG. 2 is a view showing an example of the arrangement of the image processing system according to an embodiment of the present invention.

FIG. 2 shows an example of the arrangement of the image processing system according to the embodiment of the present invention.

Note that the upper portion of FIG. 2 is a top view of the image processing system arrangement, and the lower portion of FIG. 2 is a side view of the image processing system arrangement.

X-rays emitted by an X-ray generator (X-ray focal point) 11 are transmitted through a subject (in this case, a human body) 16, and reach a 2D detector 12 after they pass through a breast plate 13 and scattered ray removal grid (not shown).

The 2D detector 12 comprises a semiconductor sensor: one pixel size is, e.g., 250×250 µm, and the sensor outer shape size is 43×43 cm. The number of pixels is, e.g., 1720×1720 pixels. Data acquired by the 2D detector 12 (projection data obtained by projecting a 3D region of the subject 16) are transferred to a reconstruction unit 14 and undergo image reconstruction. Note that a fan angle $\phi$ and cone angle are determined by the geometrical layout of the X-ray generator 11 and 2D detector 12.

Since this embodiment uses the 2D detector having a square detection surface, the fan angle equals the cone angle.

The detailed arrangement of the image processing system of this embodiment will be described below using FIG. 3.

Figure 3:
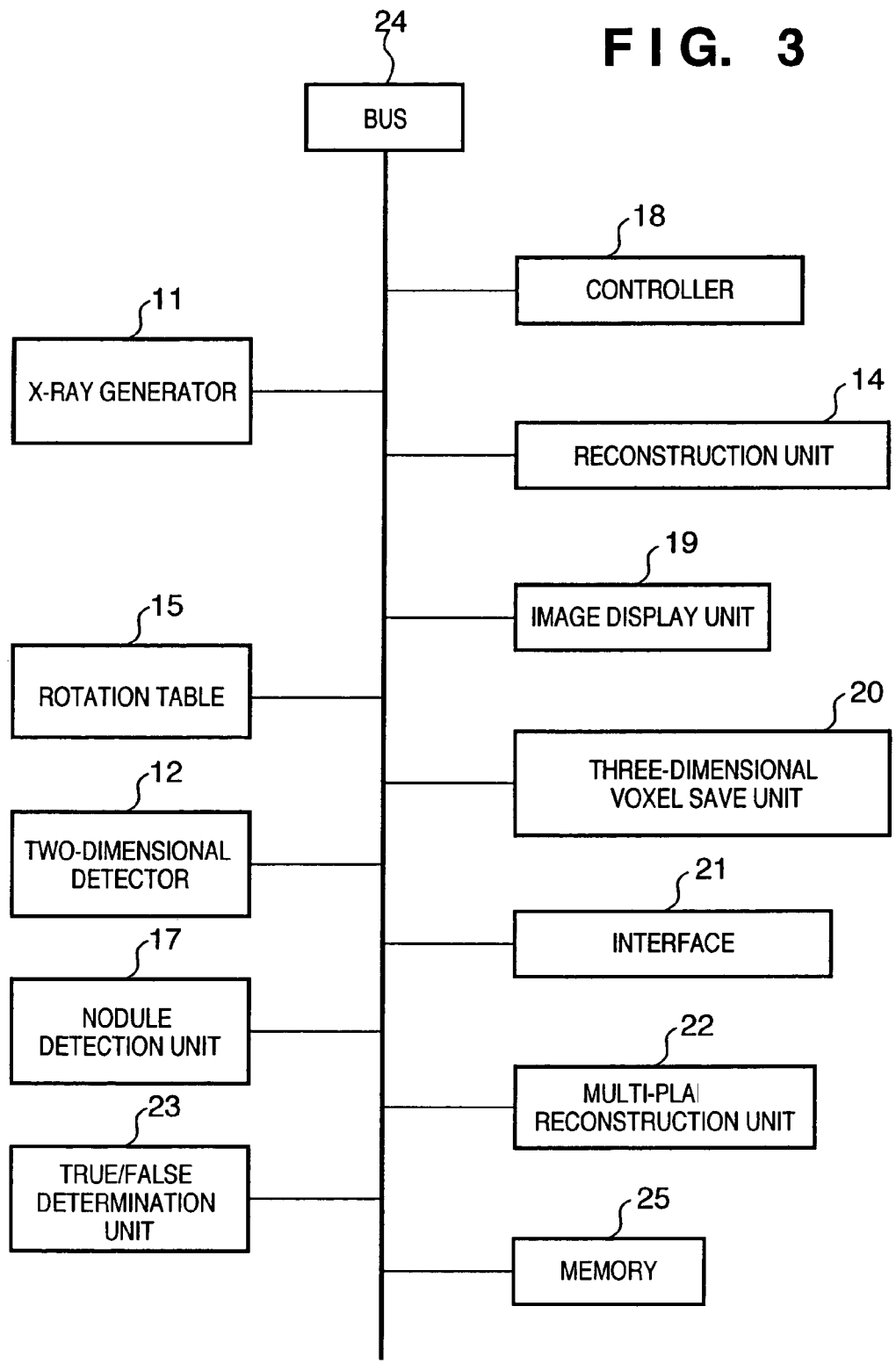
FIG. 3 is a block diagram showing the detailed arrangement of the image processing system according to the embodiment of the present invention.

FIG. 3 is a block diagram showing the detailed arrangement of the image processing system according to the embodiment of the present invention.

The entire system is implemented by a computer system. A BUS 24 can be considered as an internal bus of the computer, and control signals and data are exchanged via this BUS 24.

A controller 18 corresponds to a CPU of the computer. A memory 25 includes, e.g., a ROM, RAM, and large-capacity storage device (e.g., a hard disk or the like). The ROM stores programs and setting data required to execute various processes of this system. The RAM serves as a work area and temporary save area of data. The large-capacity storage device stores various data such as projection data, image data, and the like.

An interface 21 includes an input unit and output unit. The input unit includes, e.g., a keyboard and pointing device (mouse or input pen), and the output unit includes a display such as a CRT, LCD, or the like. An imaging start instruction is input via the input unit of the interface 21.

Upon input of the imaging start instruction, a rotation table 15 on which the subject 16 is fixed begins to rotate in accordance with an instruction from the controller 18. The controller 18 monitors an encoder signal (not shown) generated from the rotation table 15, and checks if a predetermined speed and angle are reached. When the predetermined speed and angle have been reached, the controller 18 transmits an enable signal to the X-ray generator 11 to start X-ray radiation. Note that the encoder signal is also used to determine the integration timing of data.

For example, when an encoder that generates 25000 pulses per revolution of the table is used, and projection data of 1000 views per revolution are acquired, projection data is acquired from the 2D detector 12 every 25 pulses of the encoder signal. The controller 18 counts pulses of the encoder signal to generate an integration signal every 25 pulses, thus counting an X-ray dose that reaches the 2D detector 12.

Assume that X-rays are generated continuously in this embodiment. However, the present invention is not limited to this. For example, X-ray pulses may be generated in correspondence with the integration periods of the 2D detector 12 on the basis of the encoder signal. The projection data from the 2D detector 12 are sequentially transferred to the reconstruction unit 14 via the BUS 24. Data transfer continues until the rotation table 15 rotates through a predetermined rotation angle, and a predetermined number of views (images) are acquired. Last projection data is acquired immediately after completion of X-ray radiation.

The acquired projection data are transferred to the reconstruction unit 14 to reconstruct a 3D voxel. The reconstruction unit 14 includes a pre-process, filter process, and back projection process. The pre-process includes, e.g. an offset process, LOG conversion, gain correction, and defect correction.

In the filter process, the Ramachandran function or Shepp-Logan function is popularly used. This embodiment also uses such function. Data that have been undergone the filter process are back projected by the back projection process in order to make a 3D voxel. As an algorithm from the filter process to the back projection process, for example, the Feldkamp algorithm is used. Upon completion of the back projection process, when a cross section image of the subject is reconstructed, that cross section image is displayed on an image display unit 19.

Note that the reconstruction unit 14 uses the Feldkamp algorithm as its processing algorithm. However, the present invention is not limited to such specific algorithm. As a reference associated with this Feldkamp algorithm, Feldkamp, Davis, and Kress, "Practical Cone-Beam Algorithm", J. Opt, Soc. Am. Al, 612-619, 1984 is known.

The reconstructed 3D voxel is saved in a 3D voxel save unit 20. This 3D voxel save unit 20 is implemented by, e.g., a large-capacity storage device such as a hard disk or the like. A multi-planar reconstruction unit 22 generates a predetermined number of coronal images from the 3D voxel saved in the 3D voxel save unit 20, and transfers them to a nodule detection unit 17.

The nodule detection unit 17 detects a nodule candidate from the coronal images. A plurality of nodule candidates may be detected. The nodule detection unit 17 calculates an extraction position so as to extract axial images including the nodule candidate from the 3D voxel. The multi-planar reconstruction unit 22 extracts axial images at the calculated extraction position from the 3D voxel saved in the 3D voxel save unit 20, and transfers them to a true/false determination unit 23.

The true/false determination unit 23 performs true/false determination, i.e., determines whether or not the nodule is a diagnostic image, on the basis of feature amounts on the axial images including the nodule candidates. The nodule determined as the diagnostic image is recorded as its volume on the 3D voxel save unit 20, and is displayed on the image display unit 19.

Note that the X-ray generator 11 and 2D detector 12 serve as an image sensing unit that senses a subject image in FIG. 3. Alternatively, a system that includes an independent image sensing unit may be used. In this case, the reconstruction unit 14 reconstructs a 3D voxel using 2D projection data obtained from this image sensing unit.

The processing to be executed by the image processing system of this embodiment will be described below using FIG. 4.

Figure 4:
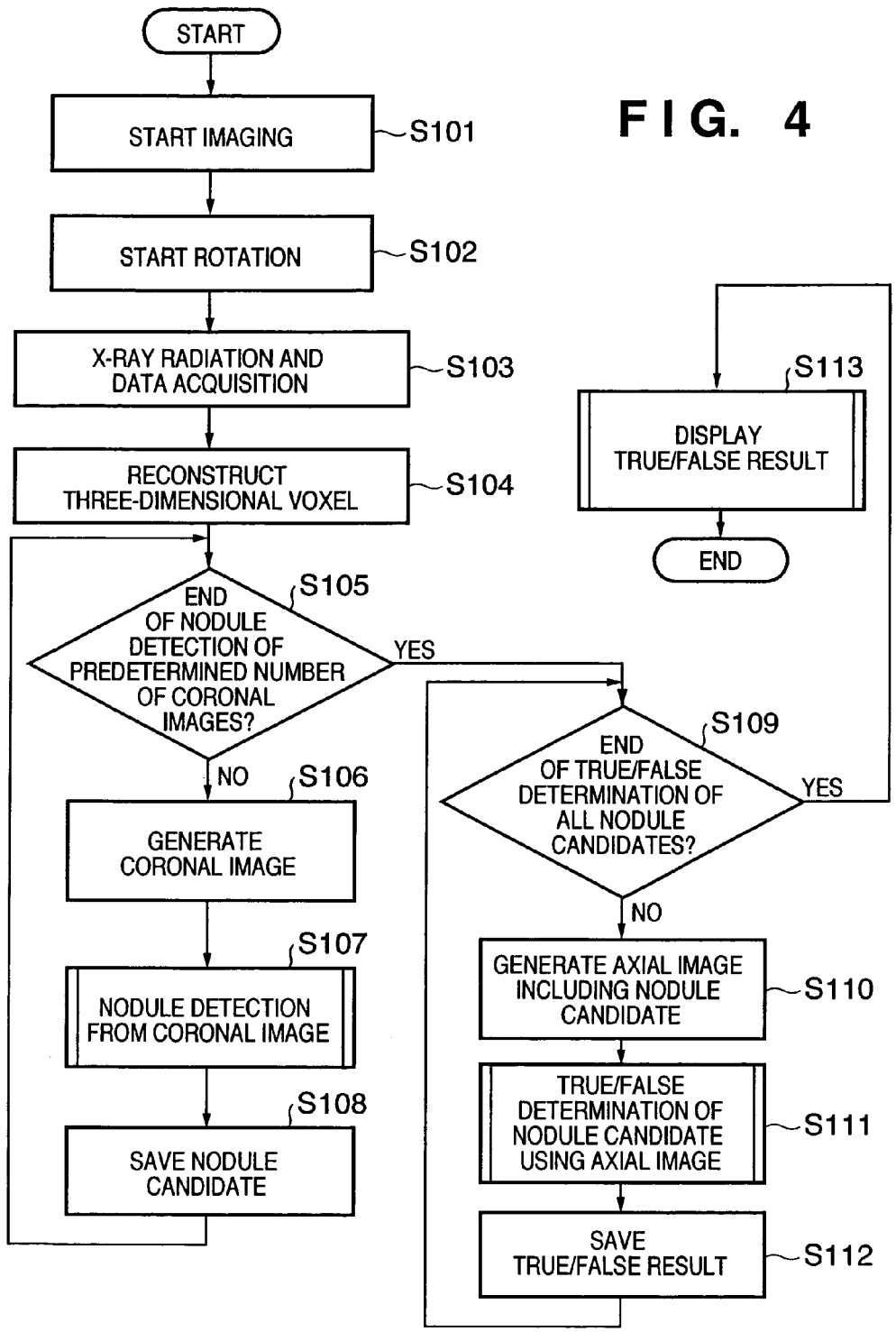
FIG. 4 is a flowchart showing the processing executed by the image processing system according to the embodiment of the present invention.

FIG. 4 is a flowchart showing the processing to be executed by the image processing system according to the embodiment of the present invention.

An imaging start instruction is input via the input unit of the interface 21 (step S101). When the imaging start instruction is input, an imaging preparation completion window (not shown) is displayed on the output unit of the interface 21. The rotation table 15 begins to rotate in response to an instruction from the controller 18 (step S102).

The controller 18 monitors an encoder signal (not shown) generated from the rotation table 15, and checks if a predetermined speed and angle are reached. When the predetermined speed and angle have been reached, the controller 18 transmits an enable signal to the X-ray generator 11 to start X-ray radiation. At the same time, the 2D detector 12 detects projection data. After the rotation table 15 has rotated through a predetermined angle and a predetermined number of views (number of projections) have been reached, the controller 18 instructs the X-ray generator 11 to stop X-ray radiation. After that, the controller 18 controls to decelerate the rotation table 15 until it stops (step S103).

The acquired data are transferred to the reconstruction unit 14, which reconstructs a 3D voxel (step S104). The reconstructed 3D voxel is saved in the 3D voxel save unit 20.

Next, it is checked if the nodule detection process of a predetermined number of coronal images as those which are to be subjected to a diagnosis aiding process from the 3D voxel saved in the 3D voxel save unit 20 is complete (step S105). If the nodule detection process of a predetermined number of coronal images is not complete yet (NO in step S105), the flow advances to step S106. On the other hand, if the nodule detection process of a predetermined number of coronal images is complete (YES in step S105), the flow advances to step S109.

Note that the coronal image generation method is determined by the slice thickness and slice pitch of a coronal image set by the input unit of the interface 21. The slice thickness and slice pitch may be pre-stored in the memory 25.

If it is determined in step S105 that the nodule detection process of a predetermined number of coronal images is not complete yet, a coronal image is generated based on the designated slice thickness and slice pitch (step S106).

The nodule detection unit 17 applies nodule detection to the coronal image (step S107).

Figure 5:
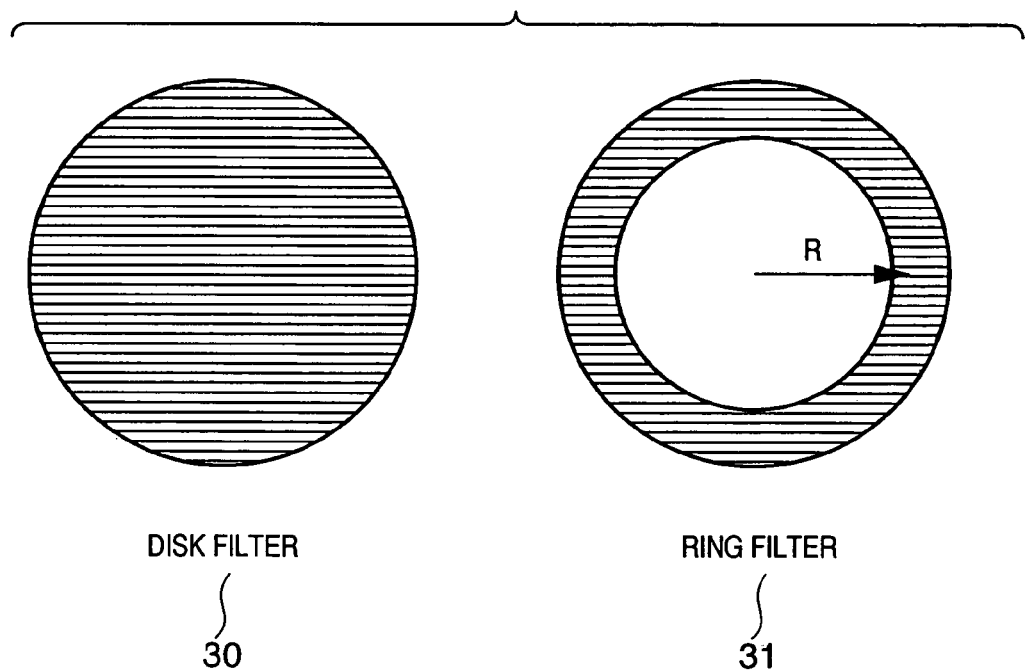
FIG. 5 shows examples of a DISK filter and RING filter according to the embodiment of the present invention.

Various nodule detection methods have been proposed. This embodiment uses, for example, a nodule detection method using a DISK filter 30 and RING filter 31 shown in FIG. 5 (e.g., see "Lung Cancer Screening CT (LSCT) Diagnosis Aiding System", Journal of CADM, VOL. 2, NO. 3, Jul., 1998 (reference 1)).

Details of the nodule detection process using the DISK filter 30 and RING filter 31 will be described below using FIG. 6.

Figure 6:
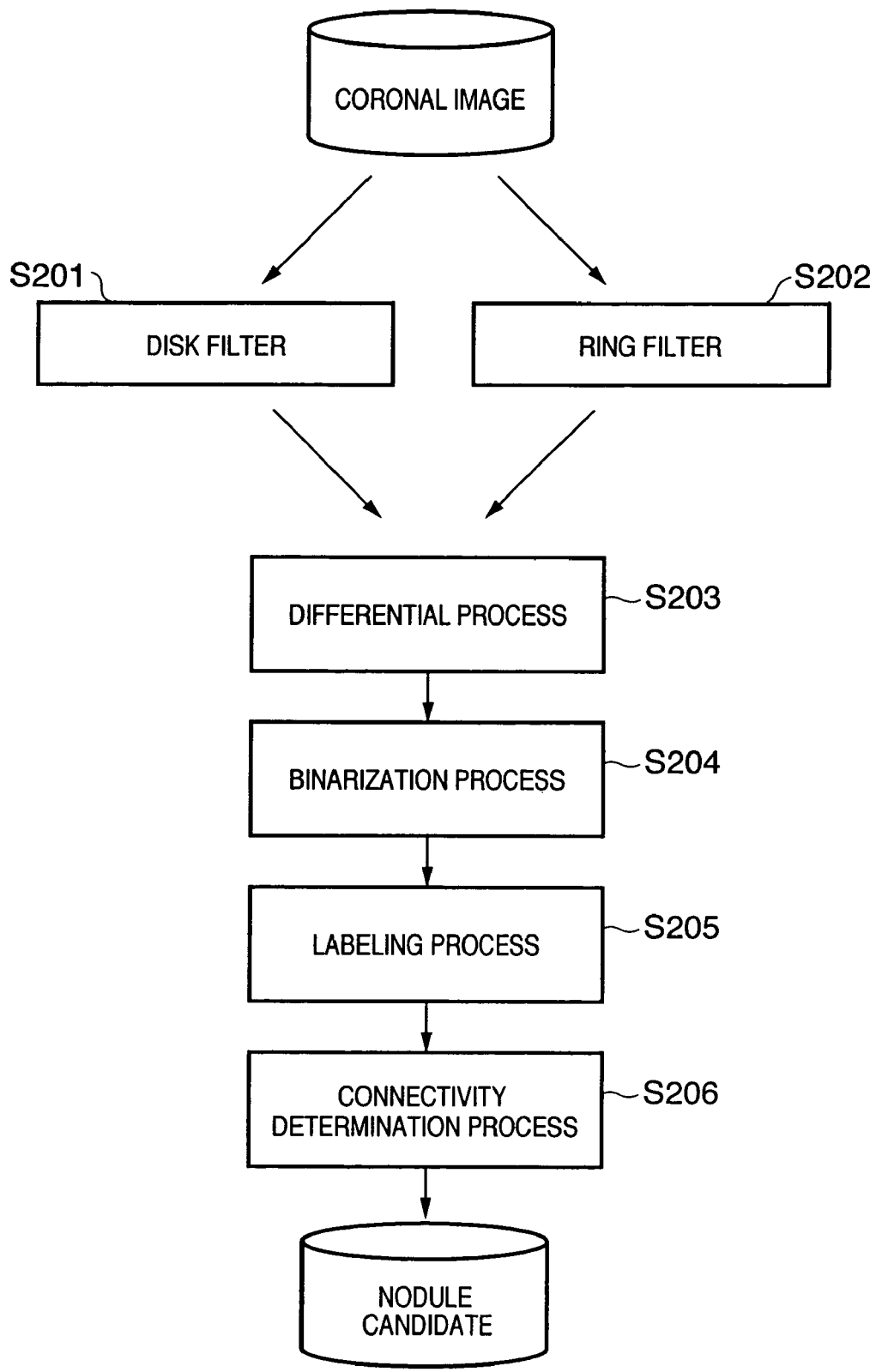
FIG. 6 is a flowchart showing details of a nodule detection process according to the embodiment of the present invention.

FIG. 6 is a flowchart showing details of the nodule detection process according to the embodiment of the present invention.

The DISK filter 30 and RING filter 31 are applied to a coronal image to be processed to generate Dilation images (steps S201 and S202), and a differential process is executed (step S203), thus emphasizing a roughly circular nodule having a radius R of the RING filter 31.

Note that the Dilation image is a kind of morphological processing (e.g., see Anil K. Jain, "Fundamentals Of Digital Image Processing", Prentice Hall, 1989, p. 384 (reference 2)).

The merit of using the DISK filter 30 and RING filter 31 is efficient removal of vein that mostly run in the coronal image in the up-and-down direction. Conventionally, the DISK filter and RING filter are applied to an axial image, as described in reference 1. However, each vein in the axial image has roughly a circular shape such as nodules, so that the above filter process misdetects most of veins as nodules.

A binarization process is applied to a differential image of the Dilation images to which the DISK filter 30 and RING filter 31 are applied (step S204). A labeling process is applied to the obtained binary image (step S205), thus removing small signals (noise) in the binary image.

Note that the image after the labeling process includes noise depending on vein and noise from a contour of a rib cage. Thus, in order to delete such noise, connectivity determination process is executed (step S206).

The connectivity determination process determines the connectivity of a nodule as a tumor on the basis of changing rates of the nodule areas and nodule centroids between neighboring coronal images. When the changing rates of the nodule areas and nodule centroids are larger than a predetermined threshold value, detection of an object which is not roughly circular is highly probable, and such candidate is excluded from the nodule candidates.

The description will revert to FIG. 4.

A nodule which is more likely to be a tumor as a result of the connectivity determination process in step S206 in FIG. 6 is saved as a tumor candidate in the memory 25 (step S108). After that, the flow returns to step S105.

If it is determined in step S105 that the detection process of nodule candidates from a predetermined number of coronal images is complete (YES in step S105), axial images corresponding to all the nodule candidates are made from the 3D voxel, and true/false determination is made to determine whether or not the nodule candidate is a diagnostic pathology image using these axial images.

It is checked if true/false determination of all the nodule candidates is complete (step S109). If true/false determination of all the nodule candidates is complete (YES in step S109), the flow advances to step S113. On the other hand, if true/false determination of all the nodule candidates is not complete yet (NO in step S109), the flow advances to step S110.

Upon generating axial images, the slice thickness and slice pitch upon generating coronal images are also used. Since the 3D shape of the nodule candidate is recognized from shapes among a plurality of coronal images, an axial image is generated to include one nodule shape (step S110). Note that the axial image to be generated in this step need not always be the one corresponding to the entire surface of an axial section of the subject, but it may be a partial axial image including the nodule candidate.

A feature amount of the nodule candidate in the axial image is calculated, and true/false determination is made to determine based on the calculation result if the nodule candidate is a diagnostic image.

Details of the true/false determination process of the nodule candidate in the axial image will be described below using FIG. 7.

Figure 7:
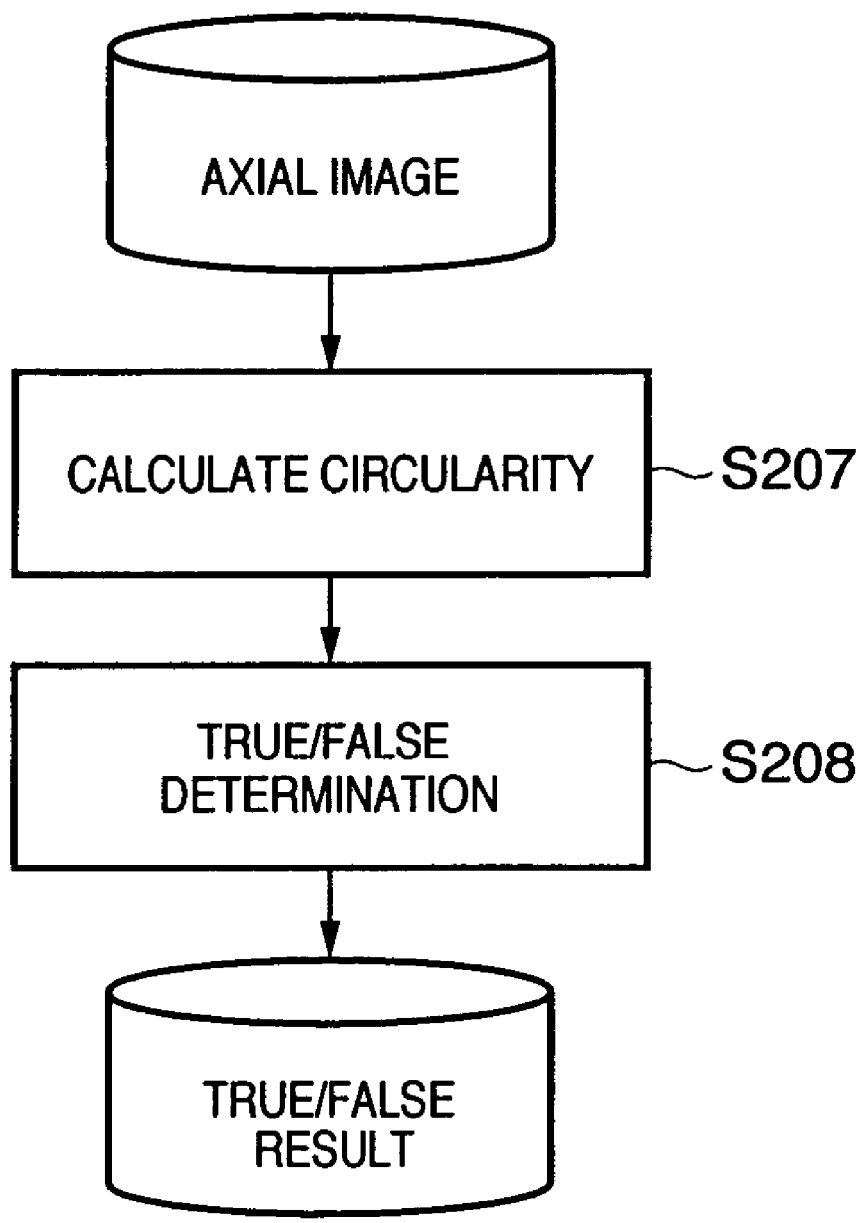
FIG. 7 is a flowchart showing details of a true/false determination process according to the embodiment of the present invention.

FIG. 7 is a flowchart showing details of the true/false determination process according to the embodiment of the present invention.

A feature amount of the nodule candidate in the axial image is calculated (step S207). In this embodiment, for example, the circularity is used as the feature amount of the nodule candidate in the axial image. However, the present invention is not limited to such specific feature amount.

Note that a vein image is erroneously detected as a nodule image in the processes in steps S201 to S206 in FIG. 6 under the condition that a vein runs from the front to the back of lungs. Under such condition, an image corresponding to a vein is detected as a linear nodule in the axial image. Hence, when the circularity is adopted as a feature amount, satisfactory true/false determination can be realized. Note that the circularity can be calculated using equations (1) and (2), as has been explained in the paragraphs of the prior art.

If the calculated circularity is smaller than a predetermined value, the probability of the image region being the nodule of a tumor is low. Also, the changing rate of the circularities between neighboring axial images is calculated, and if this changing rate is larger than a predetermined value, the probability of the image region being the nodule of a tumor is low. With this determination method, the true/false determination process is executed for one nodule candidate (step S211), and the true/false result is saved in the memory 25.

The description will revert to FIG. 4.

After the true/false determination process is executed, the determination result (true/false result) is saved in the memory 25. If the processes in steps S110 to S112 are executed for all the nodule candidates, i.e., if true/false determination for all the nodule candidates is complete (YES in step S109), the true/false results stored in the memory 25 are displayed on the image display unit 19 (step S113).

Note that the true/false result appends a true/false attribute indicating whether or not each nodule is a diagnostic image as a tumor to each nodule candidate saved in step S108. When a nodule region which is determined to be true is substituted by a specific value on the 3D voxel, since an image corresponding to a tumor can be automatically displayed upon executing multi-planar reconstruction, it is suited to a diagnostic image.

As described above, according to the present invention, since coronal images include fewer nearly circular nodules than axial images, the processing time required to detect a nodule from an image to be processed can be shortened, and the number of false-positives for a pathology (tumor) can be reduced.

The above embodiment has exemplified a case wherein coronal images are used as images which are to undergo nodule detection. In addition, other cross section images such as sagittal images, oblique images, their RAYSUM images (projection images having a thickness from one point on a 3D space, and are suited to diagnosis simultaneously done by some doctors), and the like, which can be obtained from the 3D voxel, can be used.

Note that axial images are not used in nodule detection in principle. This is because a tumor and vein are easily erroneously determined, as described above, and one characteristic feature of the present invention lies in that cross section images other than axial images are used in nodule detection.

However, axial images are preferably used in nodule detection in some cases depending on a position in a rib cage. For example, veins are observed as fine points in thin coronal images of portions near the chest wall and back wall, and in a thin sagittal image of a portion near the flank. This is because thin veins run toward the rib cage. When a nodule is formed in such portion, it is easy to find the nodule in axial images. Hence, nodule detection is preferably made first using axial images in those regions. Therefore, another embodiment of the present invention is wherein different cross section images to which nodule detection is applied are used depending on a region in a rib cage, and cross section images perpendicular to the cross section used in nodule detection are used in true/false determination.

The present invention performs nodule detection using cross section images (first cross section images) other than axial images (cross section images perpendicular to the body axis of a subject), and uses second cross section images different from the first cross section images in true/false determination of nodules detected by the nodule detection.

Various combinations of first and second cross section images are available. As more practical combinations, the following ones are used:

First cross section image: Second cross section image

| Coronal image: | Axial or sagittal image |
| Sagittal image: | Axial or coronal image |

These combinations allow to three-dimensionally determine the nodule shape. Using these combinations, nodule detection and true/false determination with higher precision can be realized.

On the other hand, first and second cross section images are selected depending on a region in the rib cage. Note that the region of the rib cage to which the method of the present invention is applied is a region near the rib cage.

| First cross section image: | Second cross section image |
| Axial image: | Coronal or sagittal image |

Other Embodiments

Note that the present invention can be applied to an apparatus comprising a single device or to system constituted by a plurality of devices.

Furthermore, the invention can be implemented by supplying a software program, which implements the functions of the foregoing embodiments, directly or indirectly to a system or apparatus, reading the supplied program code with a computer of the system or apparatus, and then executing the program code. In this case, so long as the system or apparatus has the functions of the program, the mode of implementation need not rely upon a program.

Accordingly, since the functions of the present invention are implemented by computer, the program code installed in the computer also implements the present invention. In other words, the claims of the present invention also cover a computer program for the purpose of implementing the functions of the present invention.

In this case, so long as the system or apparatus has the functions of the program, the program may be executed in any form, such as an object code, a program executed by an interpreter, or scrip data supplied to an operating system.

Example of storage media that can be used for supplying the program are a floppy disk, a hard disk, an optical disk, a magneto-optical disk, a CD-ROM, a CD-R, a CD-RW, a magnetic tape, a non-volatile type memory card, a ROM, and a DVD (DVD-ROM and a DVD-R).

As for the method of supplying the program, a client computer can be connected to a website on the Internet using a browser of the client computer, and the computer program of the present invention or an automatically-installable compressed file of the program can be downloaded to a recording medium such as a hard disk. Further, the program of the present invention can be supplied by dividing the program code constituting the program into a plurality of files and downloading the files from different websites. In other words, a WWW (World Wide Web) server that downloads, to multiple users, the program files that implement the functions of the present invention by computer is also covered by the claims of the present invention.

It is also possible to encrypt and store the program of the present invention on a storage medium such as a CD-ROM, distribute the storage medium to users, allow users who meet certain requirements to download decryption key information from a website via the Internet, and allow these users to decrypt the encrypted program by using the key information, whereby the program is installed in the user computer.

Besides the cases where the aforementioned functions according to the embodiments are implemented by executing the read program by computer, an operating system or the like running on the computer may perform all or a part of the actual processing so that the functions of the foregoing embodiments can be implemented by this processing.

Furthermore, after the program read from the storage medium is written to a function expansion board inserted into the computer or to a memory provided in a function expansion unit connected to the computer, a CPU or the like mounted on the function expansion board or function expansion unit performs all or a part of the actual processing so that the functions of the foregoing embodiments can be implemented by this processing.

As many apparently widely different embodiments of the present invention can be made without departing from the spirit and scope thereof, it is to be understood that the invention is not limited to the specific embodiments thereof except as defined in the appended claims.

CLAIM OF PRIORITY

This application claims priority from Japanese Patent Application No. 2004-117058 filed on Apr. 12, 2004, the entire contents of which are hereby incorporated by reference herein.

What is claimed is:

1. An image processing apparatus for processing a radiation image of a subject obtained by utilizing radiation, and outputting a diagnostic image, comprising:

first generation means for generating a first cross-sectional image of a first cross-section other than an axial cross-section of the subject from the radiation image;

detection means for detecting a circular shape in the first cross-sectional image as a nodule;

second generation means for generating a second cross-sectional image of a second cross-section other than the first cross-section of the subject from the radiation image, wherein the second cross-sectional image includes the nodule detected by said detection means;

calculation means for calculating a circularity of the nodule in the second cross-sectional image as a feature amount, wherein the nodule is detected by said detection means and comprises a circular shape in the first cross-section;

determination means for determining whether or not the nodule detected by said detection means is a diagnostic pathology on the basis of the feature amount calculated by said calculation means; and output means for outputting a diagnostic image including the nodule detected by said detection means on the basis of a determination result of said determination means.

2. The apparatus according to claim 1, wherein the first cross-sectional image is one of a coronal image, sagittal image, and RAYSUM image thereof of the subject.

3. The apparatus according to claim 1, wherein the second cross-sectional image is an axial image of the subject.

4. The apparatus according to claim 1, wherein when the first cross-sectional image is a coronal image of the subject, the second cross-sectional image is one of an axial image and sagittal image of the subject.

5. The apparatus according to claim 1, wherein a 3D voxel reconstructed from the radiation image is formed of isotropic pixels.

6. The apparatus according to claim 1, further comprising:
image sensing means for irradiating the subject with radiation, and sensing and outputting the radiation image of the subject.

7. A computer-readable medium storing, in executable form, a program for causing a computer to implement image processing for processing a radiation image of a subject obtained by utilizing radiation, and to output a diagnostic image, comprising:
a program code of a first generation step of generating a first cross-sectional image of a first cross-section other than an axial cross-section of the subject from the radiation image;
a program code of a detection step of detecting a circular shape in the first cross-sectional image as a nodule;
a program code of a second generation step of generating a second cross-sectional image of a second cross-section other than the first cross-section of the subject from the radiation image, and wherein the second cross-sectional image includes the nodule detected in said detection step;
a program code of a calculation step of calculating a circularity of the second cross-sectional image as a feature amount, wherein the nodule is detected by said detection means and comprises a circular shape in the first cross-section;
a program code of a determination step of determining whether or not the nodule detected in the detection step is a diagnostic pathology on the basis of the feature amount calculated in the calculation step; and
a program code of an output step of outputting a diagnostic image including the nodule detected in the detection step on the basis of a determination result in the determination step.

8. The apparatus according to claim 1, further comprising:
exclusion means for excluding the nodule from nodules used in said second generation means, when the changing rates of areas and centroids of the nodules in the images neighboring said first cross-sectional image are larger than a predetermined threshold value.

9. The apparatus according to claim 1, wherein said determination means determines that the nodule detected by said detection means is not a diagnostic pathology, when the calculated circularity is smaller than a first predetermined value or the changing rate of the calculated circularity in images neighboring said second cross-sectional image is larger than a second predetermined value.

* * * * *